US005728688A

United States Patent [19]

Labrie

[11] Patent Number: 5,728,688
[45] Date of Patent: Mar. 17, 1998

[54] THERAPEUTIC METHODS AND DELIVERY SYSTEMS UTILIZING SEX STEROID PRECURSORS

[75] Inventor: Fernand Labrie, Quebec, Canada

[73] Assignee: Endoreoherche, Inc., Quebec, Canada

[21] Appl. No.: 480,591

[22] Filed: Jun. 7, 1995

Related U.S. Application Data

[62] Division of Ser. No. 5,619, Jan. 19, 1993, abandoned.

[51] Int. Cl.$^6$ ................................................ A61K 31/56
[52] U.S. Cl. ........................................................... 514/178
[58] Field of Search ............................................... 514/178

[56] References Cited

U.S. PATENT DOCUMENTS

| | | |
|---|---|---|
| 3,472,931 | 10/1969 | Stoughton . |
| 3,551,554 | 12/1970 | Herschler . |
| 3,742,951 | 7/1973 | Zaffaroni . |
| 3,797,494 | 3/1974 | Zaffaroni . |
| 3,989,816 | 11/1976 | Jagannath . |
| 4,006,218 | 2/1977 | Tibor . |
| 4,213,978 | 7/1980 | Bodor . |
| 4,405,616 | 9/1983 | Rajadhyaksha . |
| 4,425,339 | 1/1984 | Pitchford .................. 424/239 |
| 4,496,556 | 1/1985 | Orentreich . |
| 4,518,595 | 5/1985 | Coleman . |
| 4,542,129 | 9/1985 | Orentreich . |
| 4,568,343 | 2/1986 | Leeper . |
| 4,624,665 | 11/1986 | Nuwayser . |
| 4,666,441 | 5/1987 | Andriola . |
| 4,812,447 | 3/1989 | Roberts . |
| 4,835,147 | 5/1989 | Roberts . |
| 4,956,355 | 9/1990 | Prendergast . |
| 4,978,532 | 12/1990 | El-Rashidy .................. 424/448 |
| 5,047,244 | 9/1991 | Sanvordeker et al. . |
| 5,051,260 | 9/1991 | Chess . |
| 5,064,654 | 11/1991 | Berner . |
| 5,071,644 | 12/1991 | Viegas . |
| 5,071,657 | 12/1991 | Oloff . |
| 5,116,828 | 5/1992 | Miura et al. . |
| 5,135,480 | 8/1992 | Bannon . |
| 5,154,922 | 10/1992 | Govil . |
| 5,162,037 | 11/1992 | Whitson . |
| 5,362,720 | 11/1994 | Labrie .................. 514/169 |

FOREIGN PATENT DOCUMENTS

| | | |
|---|---|---|
| 0127829 | 5/1984 | European Pat. Off. . |
| 279982 | 11/1987 | European Pat. Off. . |
| 1584879 | 1/1970 | France . |
| 2534911 | 2/1977 | Germany . |
| 2948733 | 12/1978 | Germany . |
| 505372 | 1/1975 | Japan . |
| 66924 | 6/1973 | Romania . |
| 6806112 | 10/1967 | South Africa . |
| 1246639 | 9/1971 | United Kingdom . |
| 2185187 | 6/1986 | United Kingdom . |
| 2204490 | 11/1988 | United Kingdom . |
| 90/10462 | 3/1990 | WIPO . |
| 93/00070 | 6/1992 | WIPO . |

OTHER PUBLICATIONS

Batra, et al., *J. Urol.*, 129(2):418–420 (1983).
Bayliss, et al., *An Illustrated Dictionary of Dermatologic Syndromes*, Parthenon Publ. Group, NY, 1994, p. 243.
Peillon, et al., *Ann. Endo.*, 26(4):419–28 (1965).
*Am. J. Nurs.*, 70:2634 (1970).
Li, et al., *British J. of Cancer*, 41:123–129 (1980).
Araki, *Kuramu Medical Journal*, 28:35–43 (1981).
Berne, et al., *Physiology*, C.V. Mosby Co., St. Louis (1983).
*Biological Abstracts*, 70:52322 (1980).
Labrie, et al., *J. of Clinical Endo. & Metab*, 82(8):2403–2409 (1997).
Labrie, et al., *J. of Clinical Endo. & Metab*, 82:(8)2396–2402 (1997).
Labrie, et al., "Signal Tranduction in Testicular Cells: Basic and Clinical Aspects, Ernst Schering Research Foundation QWOrkshop," Supplement 2, Ed. Hansson, Springer–Verlag, pp. 185–218 (1996).
Labrie, et al., *Steroids*, 62:148–158 (1997).
Labrie, et al., *N.Y. Academy of Sciences*, 774:16–28 (1995).
Labrie, et al., *J. of Clinical Endo. & Metab*, 82(10):1–7 (1997).
Luo, et al., *Endocrinology*, 138(8):3387–3394 (1997).
Labrie, et al., *DHEA and Sex Steroids*, Society for Endocrinology (1996).
Reynolds, "Martindale The Extra Pharmacopoeia" —Prasterone, 29th Edition (1989).
CA, 96:46434c (1982).
Beamer, et al., *Cancer Research*, 48:2788–2792 (1988).
Marslew, et al., *Maturitas*, 12:7–16 (1991).
Djerassi, et al., *J. Org. Chem.*, 27:1112 (1962).
Edman, *The Menopause*, p.222 (1983).
Ringold, et al., *J. Am. Chem. Soc.*, 78:816 (1956).
Wilson, et al., *Williams Textbook of Endocr.*, pp. 1033–1048 (1992).
Forest, *Andregens in Childhood* (19):104–120 (1989).
Meunier, et al., *Histological heterogeneity...treatment*,pp. 293–301 (1980).

(List continued on next page.)

*Primary Examiner*—Richard L. Raymond
*Attorney, Agent, or Firm*—Ostrolenk, Faber, Gerb & Soffen, LLP

[57] ABSTRACT

Sex steroid precursors such as dehydroepiandrosterone and dehydroepiandrosterone sulphate, and compounds converted in vivo to either of the foregoing, are utilized for the treatment of vaginal atrophy, hypogonadism, diminished libido, loss of collagen or connective tissues in the skin, and, in combination with an estrogen and/or progestin, for the treatment of menopause. The precursors may be formulated for percutaneous or transmucosal administration. Gels, solutions, lotions, creams, ointments and transdermal patches for the administration of these precursors are provided, as are certain pharmaceutical compositions and kits which can be used for the prevention and treatment of a wide variety of conditions related to decreased secretion of sex steroid precursors by the adrenals.

3 Claims, No Drawings

OTHER PUBLICATIONS

Mortola, *Journal of Clinical Endo. and Metab.* 71(3) (1990).

Bird, *Clinical & Investigative Medicine* 7(2):119–122 (1984).

Roberts, et al., *Biological Role of DHEA* (1990).

Belisle, et al., *Journal of Clinical Endocrinology & Metabolism*, 45(3) (1977).

Poulin, et al., *Br. Cancer Res. Treat.* 13:265–276 (1989).

Haning, Jr., et al., *Journal of Clinical Endocrinology & Metabolism*, 69 (5) (1989).

Abou–Gharbia, et al., *J. Pharm. Sci.* 73:1643–5 (1984).

Adams, *Mol. Cell. Endo.* 41:1–17 (1985).

Aloia, et al., *Arch. INt. Med.* 143:1700–1704 (1984).

Arad, et al., *Arteriosclerosis* 2:159–166 (1989).

Baran, et al., *Calcif. Tissue Res.* 26:103–106 (1978).

Bélanger, et al., *Annals of the NY Acad Sci.* 586:93–100 (1990).

Brownsey, B.; Cameron, E. H. D.; Griffiths, K.; Gleave, E. N.; Forrest, A.P.M.; Campbell, H. (1972) Plasma dehydreopiandrosterone sulphate levels in patients with benign and malignant breast disease. Europ. J. Cancer. 8:131–137.

Bulbrook RD; Hayward JL; Spicer CC; Thomas BS (1962) Abnormal excretion of urinary steroids by women with early breast cancer. The Lancet. Dec.:1238–1240.

Bulbrook RD; Hayward JL; Spicer CC; Thomas CS (1962) A comparison between the urinary steroid excretion of normal women and women with advanced breast cancer. The Lancet. Dec.:1235–1240.

Bulbrook RD; Hayward JL; Spicer CC (1971) Relation between urinary androgen and corticoid excretion and subsequent breast cancer. The Lancet. Aug.:395–398.

Bundgard H (1991) Design and application of prodrugs. In: A textbook of drug design and development (P. Krogsgaard-–Larsen, H. Bundgard, eds), Harwood Academic Publishers GmfH, Chur:Switzerland. pp.113–191.

Cameron EHD; Griffiths K; Gleave EN; Stewart HJ; Forrest APM; Campbell H (1970) Benign and malignant breast disease in south wales: a study of urinary steroids. Br. Med. J. 4:768–771.

Challis JRG; Heap RB (1970) Steroid mono– and diheptafluorobutyrates: preparation, purification and estimation. J. Chromatogr. 50:228–238.

Cleary MP; Zisk J (1983) Effect of dehydroepiandrosterone (DHEA) in adult zucker rats. Fed. Proc. 42:536 (abst. 1433).

Colevard DS; Eriksen EF; Keeting EM; Lubahn DB; French FS; Riggs BL; Spelsberg TC (1989) Identification of androgen receptors in normal human osteoblast–like cells. Proc Natl. Acad Sci. USA. 86: 854–857.

Dauvois S; Geng CS; Lévesque C; Mérand Y;Labrie F (1991) Additive inhibitory effects of an androgen and the antiestrogen EM–170 on estradiol–stimulated growth of human ZR–75–1 breast tumors in athymic mice. Cancer Res. 54:3131–3135.

Deutsch, S.; Benjamin, F.; Seltzer, V.; Tafreshi, M.; Kocheril, G.; Frank, A. (1987) The correlation of serum estrogens and androgens with bone density in the late postmenopause. Int. Gynecol. Obstet. 25:217–222.

Drefahl G (1982) Derivatisierung von dexran mit p–Amino–benzoesaure–androstenolonester. Z. Chem. 22:178.

Druzgala et al. (1991) J. Steriod Biochem. Molec. Biol. 38:149–154.

Edman CD (1983) Estrogen replacement therapy. In: The Menopause Springer Verlag: New York. 6:pp. 77–84.

Eriksen, E. F.; Colvard, D. S.; Berg, N.J.; Graham, M. L.; Mann, K. G.; Spelsbert, C.; Riggs, B.L. (1988) Evidence of estrogen receptors in normal human osterblast–like cells. Science. 241:84–86.

Finkelstein JS, Klibanski A; Neer RM; Greenspan SL; Rosenthal DI; Crowley WF (1987) Osteoporosis in men with idiopathic hypogonadotropic hypogonadism. Ann. Int. Med. 106:354–361.

Flood JF; Roberts E (1988) Dehydroepiandrosterone sulfate improves memory in aging mice. Brain Res. 448:178–181.

Friend DR (1990) Critical Reviews in Therapeutic Drug Carrier Systems. In: Transdermal delivery of contraceptives 7: pp. 149–186.

Furlaneto RW; Underwood LE; Van Wyk JJ (1977) Estimation of somatonmedin–C levels in normals and patients with pituitary disease by radioimmunoassay. J. Clin. Invest 60:648–657.

Giusti G; Gonnelli P; Borrelli D; Fiorelli G; Forti G; Pazzagli M; Serio M (1975) Age–related secretion of androstenedione, testosterone and dihydrotestosterone by the human testis. Exp. Geront. 10:241–245.

Gomes, P.; Cassanas, G.; Halberg, F.; Hermida, R.; Robel, P.; Baulieu, E. E.; Lakatua, D.; Haus, E. (1988) Taux sanguinde sulfate de la déhydroépiandrostérone (DHEA–S) et risque de cancer du sein. C.R. Acad. Sci. Paris. t 306, série III:261–264.

Gordon, G. B.; Bush, D E.; Weisman, H.F. (1988) Reduction of atherosclerosis by administration of dehydroepiandrosterone. J. Clin. Invest. 82:712–720.

Gordon, G. B.: Helzlsourer, K. J.; Comstock, G.W. (1991) Serum levels of dehydroepiandrosterone and its sulfate and the risk of developing bladder cancer. Cancer Res. 51:1366–1369.

Haning, R. V.; Flood, C. A.; Hackett, R. J.; Loughlin, J. S.; McClure, N.; Longscope, C. (1991) Metabolic clearance rate of dehydroepiandrosterone sulfate, its metabolism to testosterone, and its intrafollicular metabolism to dehydroepiandrosterone, androstenedione, testosterone, and dihydrotestosterone in vivo. J. Clin. Endocr. Metab. 72:1088–1095.

Hanson JR; Reese PB (1985) Neighbouring group participation in the allylic oxidation of a delta5–steroid. J. Chem. Soc. Perkin Trans. 1:647–649.

Heublein G; Heublein B; Schmidt B; Koch U; Brendel E; Schutz H (1984) Darstellung polymer steroidacetale und steroidester. Acta Polym. 35:673–7.

Hollo, I.; Feher, T.; Szucs, J. (1970) Serum dehydroepiandrosterone, androsterone and cortisol level in primary postmenopausal and other type osteoporosis. Acta Med. Hung. 27:155–160.

Hollo, I.; Fehér T. (1964) Studies on postmenopausal osteoporosis. I. Urinary excretion of 17–ketosteroid fractions in postmenopausal osteoporsis. Acta Med. Hung. 20: 233–247.

Hollo, I.; Szalay, F.; Szucs, J.; Boross, M. (1976) Osteoporosis and androgens. Lancet. 1357.

Jarosz S; Zamoiski A (1982) Asymetric photocycloaddition between furan and optically active ketones. Tetrahedron. 38:1453–1456.

Katz J; Finlay TH; Banerjee S; Levitz M (1987) An estrogen–dependent esterase activity in MCF–7 cells. J. Steroid Biochem. 26:687–692.

Kent, S. (1982) DHEA: "Miracle" drug? Geriatrics. 37:157–161.

Khaidem IS; Singh LR (1988) Synthesis of steroidal [C–16, 17–e]–fused dihydro–a–pyrones. Indian J. Chem. 27B: 850–1.

Koller C; Buri P (1987) Propriét és et intér êt pharmaceutique des gels thermoréversibles `` base de poloxamers et polyxamines. S.T.P. Pharma. 3:115–124.

Komm, B.S.; Terpening, C. M.; Benz, D. J.; Graeme, K . A.; Gallegos, A.; Korc, M.; Greene, G.L.; O'Malley, B. W.; Haussler, M.R. (1988) Estrogen binding, receptor mRNA, and biologic response in osteoblast–like ostersarcoma cells. Science. 241:81–84.

Korenman SG (1992) Sexual dysfunction. In: Williams Textbook of Endocrinology (Wilson JD, Foster DW, eds), WB Saunders Co: Philadelphia. pp. 1033–1048.

Labrie, C.; Bélanger, A.; Labrie, F. (1988) Androgenic activity of dehydroepiandrosterone and androstenedione in the rat ventral prostate. Endocrinology. 123:1412–1416.

Labrie, F. (1991) Intracrinology. Mol. Cell. Endocrinol. 78:C113–C118.

Labrie, F.; Dupont, A.; Bélanger, A. (1985) Complete blockade for the treatment of prostate cancer. In: Importance Advances in Oncology (De Vita, V. T., Hellman, S., Rosenberg, S.A., eds), J.B. Lippincott Co.: Philadelphia. pp. 193–217.

Leszczynski DE; Schafer RM; Perkins EG: Jerrell JP; Kummerow FA (1989) Esterification of dehydroepiandrosterone by human HDL. Biochim. Biophys. Acta. 1014:90–97.

Leszczynski DE; Schafer RM (1991) Metabolic conversion of six steroid hormones by human plasma high–density lipoprotein. Biochem. Biophys. Acta. 1083:18–28.

Lewis JG; Ghanadian R; Chisholm GD (1976) Serum 5α–dihydrotestosterone and testosterone changes with age in man. Acta Endocrinologica. 82:444–448.

Lippman, M.E. (1983) Antiestrogen therapy of breast cancer. Semin. Oncol. 10:11–19.

Marshall DH; Crilly R; Nordin BED (1978) The relation between plasma androstenedione and oestrone levels in untreated and corticosteroid–treated post–menopausal women. Clin. Endocrinology. 9:407–412.

Migeon CJ; Keller AR; Lawrence B; Shepard TH (1957) Dehydreopiandrosterone and androsterone levels in human plasma effect of age and sex; day–to–day and diurnal variations. J. Clin. Endocr. Metab. 17:1051–1062.

Need, A.G.; Horowitz, M.; Moris, H.A. Walker, C.J.; Nordin, B.E.C. (1987) Effects of nadrolone therapy on forearm bone mineral contant in osteoporosis. Clin. Orthop. 225:273.

Nieschlag E; Lammers U; Freischem CW; Langer K; Wickings EJ (1982) Reproductive functions in young fathers and grandfathers. J. Clin. Endocr. Metab. 55:676–681.

Nordin BED; Aaron J; Speed R; Crilly RG (1981) Bone formation and resorption as the determinants of trabecular bone volume in postmenopausal osteoporosis. The Lancet. Aug.:277–279.

Nordin, B.E.C.; Robertson, A.; Seamark, R.F.; Bridges, A.; Philcox, J.C.; Need, A.G.; Horowitz, M.; Morris, H.A.; Deam, S. (1985) The relation between calcium absorption, serum dehydroepiandrosterone, and vertebral mineral density in postmenopausal women. J. Clin. Endocr. Metab. 60:651–657.

Odell, W.D.; Swerdloff, R.S. (1976) Male hypogonadism. West. J. Med. 124: 446–475.

Parish EJ; Chitrakorn S (1985) Benzotriazole–mediated selective chromium(vi)oxidations. Synth. Commun. 15:393–399.

Parker C.R.; Simpson, E.R.; Bilheimer, D.W.; Leveno, K.; Carr, B.R.; MacDonald P.C. (1980) Inverse relation between low–density lipoprotein–cholesterol and dehydroisoandrosterone sulfate in human fetal plasma. Science. 208:512–514.

Pettit GR; Kamano Y; Drasar P; Inoue M; Knight JC (1987) Synthesis of bufalitoxin and bufotoxin. J. Org. Chem. 52:3573–3578.

Pinelli A; Nair PP (1969) Gas–liquid chromatographic separation of steroids and their derivatives on a dual component column of high thermal stability. J. Chromatogr. 43:223–228.

Pohlmann JLW; Elser W; Boyd PR (1971) Structure dependence of cholesteric mesophases II. Mol. Cryst. Liquid Cryst. 13:243–254.

Poulin, R.; Baker, D.; Labrie, F. (1988) Androgens inhibit basal and estrogen–induced cell proliferation in the ZR–75–1 human breast cancer cell line. Breast Cancer Res. Treatm. 12:213–225.

Poulin, R.; Labrie, F. (1986) Stimulation of cell proliferation and estrogenic response by adrenal C19–Δ5 –steroids in the ZR–75–1 human breast cancer cell line. Cancer Res. 46:4933–4937.

Reber F; Reichstein T (1945) d–galaktose–3–methylather. Helv. Chim. Acta. 28:1164–1176.

Riggs, B. L.; Wahner, H. W.; Dunn, W.L.; Mazess, R. B.; Offord, K.P.; Melton, L.J. (1987) Differential changes in bone mineral density of the appendicular and axial skeleton with aging. J. Clin. Invest. 67:328–335.

Riva S; Bovara R; Ottolina G; Secundo F; Carrea G (1989) Regioselective acylation of bile acid derivatives with candida cylindreacca lipase in anhydrous benzene. J. Org. Chem. 54:3161–3164.

Rose DP; Stauber P; Thiel A; Crowley JJ: Milgrath JR (1977) Plasma dehydroepiandrosterone sulfate, androstenedione and cortisol, and urinary free cortisol excretion in breast cancer. Europ. J. Cancer. 13:43–47.

Schaefer (1982) (Schaefer, Zesch and Stuttgen, eds), Springer–Verlag: Berlin, Heidelberg, New York. 896.

Schwartz, A.G. (1979) Inhibition of spontaneous breast cancer formation in female C3H (Avy/a) mice by long–term treatment with dehydroepiandrosterone. Cancer Res. 39:1129–1132.

Seevers RH; Groziak MP; Weichert JP; Schwendner SW; Szabo SM; Longino MA; Counsell RE (1982) Potential tumor– or organ–imaging agents. 23. Sterol esters of iopanoic acid. J. Med. Chem. 25:1500–1503.

Silberberg M; Silberberg R (1971) Steroid hormones and bone. In: The biochemistry and physiology of bone (Bourne GH, ed), Academic Press: New York. Vol. II, 2nd ed.: pp.401–484.

Sledge, G.W.; McGuire, W.L. (1983) Steroid hormone receptors in human breast cancer. Adv. Cancer Res. 38:61–75.

Smith, D.C.; Walker, M.S. (1977) Changes in plasma steroids and bone density in Klinefelter's syndrome. Calcif. Tissue Res. 22:225–228.

Thijssen et al. (1975) Androgen in postmenopausal breast cancer: Excretion, production and interaction with estrogens. J. Steroid Biochem. 6:729–734.

Urist, M.R.; Vincent, P. J. (1961) The excretion of various fractions of the 17–ketosteroids in the urine in women with postmenopausal or senile osteoporosis. J. Clin. Orthop. 18:199–208.

Verhas, M.; Schoutens, A.; L'Hermite–Baleriaux, M.; Dourov, N.; Verschaeren, A.; Mone, M.; Heilporn, A. (1986) The effect of orchidectomy on bone metabolism in aging rats. Calif. Tissue Res. 39:74–77.

Vermeulen A; Deslypere JP; Schelfhout W; Verdonck L; Rubens R (1982) Adrenocortical function in old age: response to acute adrenocorticotropin stimulation. J. Clin. Endocrinol. Metab. 54:187–191.

Vermeulen A; Verdonck L (1976) Radioimmunoassay of 17β–hydroxy–5α–androstan–3–ones, 4–androstene–3, 17–dione, dehydroepiandrosterone. 17–hydroxprogesterone and progesterone and its application to human male plasma. J. Steroid Biochem. 10:1–10.

Wang DY; Bulbrook RD; Herian M; Hayward JL (1974) Studies on the sulphate esters of dehydroepiandrosterone and androsterone in the blood of women with breast cancer. Europ. J. Cancer. 10:477–482.

Weisz I (1986) Selective reactions of some steroids with diethyl dicarbonate. Arch. Pharm. (Weinheim, Ger.). 319:952–953.

Wink CS; Felts WJL (1980) Effects of castration on the bone structure of male rats: a model of osteoporosis. Calcif. Tissue Int. 32:77–82.

Wittliff, J.L. (1984) Steroid–hormone receptors in breast cancer. Cancer. 53:630–643.

Yamashita H; Kurosawa Y (1975) Production of 16α–hydroxydehydroepiandrosterone. Agric. Biol. Chem. 39:2243–2244.

Yen, T.T.; Allan, J.A.; Pearson, D.V.; Action, J.M. (1977) Prevention of Obesity in Avy/a mice by dehydroepiandrosterone. Lipids. 12:409–413.

Zumoff B; Strain GW; Kream J; O'Connor J; Rosenfeld RS; Levin J; Fukushima DK (1982) Age variation of the 24–hour mean plasma concentrations of androgens, estrogens, and gonadotropins in normal adult men. J. Clin. Endocrinol. Metab. 54:534–538.

Rote Liste, Bundesverband Der Pharmazeutischen Industrie E.V. 1992 —Gynodian Depot.

STN International, Karlsruhe File Medline, AN=91262935 G.A. Hauser 1990.

The Merck Index, 9th Ed., 1976, p. 376, #2846.

Chem Abst. 76: 54671g (1971).

Schwartz, et al., *Advances in Cancer Research* 51:391–423 (1989).

Gordon, et al., *Advances in Enzyme Regulation* 26:355–383 (1987).

Parker, et al., *Science* 208:512 (1980).

Nestler, et al., *J. Clin. Endo. and Metab.* 66(1):57–61 (1988).

Orentreich, et al., *J. Clin. Endo. and Metab.* 59(3):551–555 (1984).

Drucker, et al., *J. Clin. Endo. and Metab.* 35:48–54 (1979).

Welle, et al., *J. Clin. Endo. and Metab.* 71(5)1259—1264 (1991).

Lacroix, et al., *J. Steroidal Biochem.* 28(3):317–325 (1987).

Buster, et al., *American J. of Obstet. & Gynecol.* pp. 1163–1170 (1992).

Barrett–Conner, et al., *New Eng. J. of Med.* 315:1519–1524 (1987).

Coleman, et al., *Diabetes* 33:26–32 (1984).

Sunderland, et al., *The Lancet* p.570 (1989).

Regelson, et al., *Annal —NY Acad. of Sci.* 521:260–273 (1988).

Thoman, et al., *Adv. in Immunology* 46:221–222 (1989).

Compendium of Patient Information (1983).

THERAPEUTIC METHODS AND DELIVERY SYSTEMS UTILIZING SEX STEROID PRECURSORS

This is a division of application Ser. No. 08/005,619, filed Jan. 19, 1993, now abandoned.

BACKGROUND OF THE INVENTION

This invention relates to a method for preventing and/or treating vaginal atrophy, hypogonadism, diminished libido and menopause in susceptible warm-blooded animals including humans involving administration of dehydroepiandrosterone (DHEA), dehydroepiandrosterone-sulfate (DHEA-S) or compounds converted in vivo to either and to pharmaceutical products for delivery of active ingredient(s) useful to the invention.

Primates are unique in having adrenals that secrete large amounts of the precursor steroid dehydroepiandrosterone (DHEA) and especially DHEA-sulfate (DHEA-S), which are converted into androstenedione ($\Delta^4$-dione) or androstene-diol ($\Delta^5$-diol) and then into potent androgens and estrogens in peripheral tissues (Adams, Mol. Cell. Endocrinol. 41: 1–17, 1985; Labrie et al., in Important Advances in Oncology (de Vita S., Hellman S., Rosenberg S. A., eds), J. B. Lippincott, Philadelphia Pa., pp 193–200, 1985). DHEA-S, the major steroid present in blood of both men and women is converted into DHEA and $\Delta5$-diol in peripheral tissues, thus maintaining a close correlation between the concentration of these three steroids in the blood (Adams, Mol. Cell. Endocrinol. 41: 1–17, 1985). Depending upon the relative activities of 17β-hydroxysteroid dehydrogenase (17β-HSD), aromarase and 5α-reductase, DHEA or its derivatives will be preferentially converted into androgens and/or estrogens.

The low serum values of DHEA and DHEA-S found at birth persist up to six years of age. Usually, during the 7th year of age, serum levels of these two steroids increase and continue to rise until age 16 in both boys and girls (Orentreich et al., J. Clin. Endocr. Metab. 59: 551–555, 1984). A further increase is then seen in males, who typically reach maximal levels between 20 and 24 years of age. In women, there is usually no further increase after 16 years. DHEA and DHEA-S decrease with aging in both men and women (Vermeulen and Verdoreck, J. Steroid Biochem. 7: 1–10, 1976; Vermeulen et al., J. Clin. Endocr. Metab. 54: 187–191, 1982). In fact, at 70 years of age, serum DHEA-S levels are at approximately 20% of their peak values while they decrease by up to 95% by the age of 85 to 90 years (Migeon et al., J. Clin. Endocr. Metab. 17: 1051–1062, 1957). The 70% to 95% reduction in the formation of DHEA-S by the adrenals during aging results in a dramatic reduction in the formation of androgens and estrogens in peripheral target tissues, thus resulting in a marked decrease in the biochemical and cellular functions induced by sex steroids.

In addition to the decrease in DHEA-S formation, in men, a progressive decrease in the concentration of testosterone in the spermatic vein (Giusti et al., Exp. Gerontol. 10: 241–245, 1975) as well as in plasma (Lewis et al., Acta Endocrinol. 82: 444–448, 1976; Zumoff et al., J. Clin. Endocr. Metab. 54: 534–538, 1982) has been observed after the age of 60–70 years. Such data, however, have been the subject of controversy (Nieschlag et al., J. Clin. Endocr. Metab. 55: 676–681, 1982). In postmenopausal women, serum testosterone levels are lower than during reproductive life (Forest M. G., Physiological changes in circulating androgens, in Androgens in Childhood (Forest M. G., ed), Karger Basel, p. 104–129, 1989).

The skin is an important site of sex steroid formation and its function is known to be regulated by sex steroids. Sex steroids can act directly in the skin or may stimulate growth hormone and prolactin secretion by the anterior pituitary gland. Skin atrophy is in fact known to occur in growth hormone deficiency, probably through a secondary decrease in insulin-like growth factor (IGF-1) secretion. Serum growth hormone (GH) and insulin-like growth factor (IGF-1) levels are known to be reduced in aging men and women.

Plasma DHEA-S concentration has been suggested as a predictor of osteoporosis (Nordin et al., J. Clin. Endocr. Metab. 60: 651–657, 1985; Deutsch et al., Int. J. Gynecol. Obstet. 25: 217–220, 1987). Serum DHEA has in fact been found to be significantly lower in osteoporotic compared to normal subjects (Nordin et al., J. Clin. Endocr. Metab. 60: 651–657, 1985). Low tissue $\Delta4$-dione is also likely to accompany low DHEA-S levels. Since $\Delta4$-dione is the precursor of estrone which is a main source of estradiol in postmenopausal women (Marshall et al., Clin. Endocrinol. 9: 407, 1978), such secondary low levels of estrogens are likely to be involved in osteoporosis (Nordin et al., Lancet 2: 277, 1981).

As another mechanism, low serum DHEA-S levels resulting in low formation of androgens in peripheral tissues could also result in low bone formation, a characteristic of postmenopausal osteoporosis (Meunier et al., in Histological heterogeneity of apparently idiopathic osteoporosis and treatment (DeLuca H. F., Frost H. M., Jee W. S. S., Johnston Jr C. C., Parfitt A. M., eds), University Park Press, Baltimore, p. 293). In fact, Deutsch et al. (Int. J. Gynecol. Obstet. 25: 217–222, 1987) have found a significant correlation between serum DHEA-S and androstenedione levels and osteoporosis in late postmenopausal women while no correlation was found between serum estrogens and bone density, thus suggesting a major importance of androgens in postmenopausal bone loss.

Studies in animals have shown that androgen deficiency leads to osteopenia while testosterone administration increases the overall quantity of bone (Silverberg and Silverberg, 1971; See Finkelstein et al., Ann. Int. Med. 106: 354–361, 1987). Orchiectomy in rats can cause osteoporosis detectable within 2 months (Winks and Felts, Calcif. Tissue. Res. 32: 77–82, 1980; Verhas et al., Calcif. Tissue Res. 39: 74–77, 1986).

As mentioned earlier, adrenal androgen levels have been found to be reduced in osteoporosis (Nordin et al., J. Clin. Endocr. Metab. 60: 651, 1985). Moreover, elevated androgens in postmenopausal women have been shown to protect against accelerated bone loss (Deutsch et al., Int. J. Gynecol. Obstet. 25: 217–222, 1987; Aloia et al., Arch. Int. Med. 143: 1700–1704, 1983). In agreement with such a role of androgens, urinary levels of androgen metabolites are lower in postmenopausal symptomatic menopausis than in matched controls and a significant decrease in conjugated dehydroepiandrosterone (DHEA) was found in the plasma of osteoporotic patients (Hollo and Feher, Acta Med. Hung. 20: 133, 1964; Urist and Vincent, J. Clin. Orthop. 18: 199, 1961; Hollo et al., Acta Med. Hung. 27: 155, 1970). It has been suggested that postmenopausal osteoporosis results from both hypoestrogenism and hypoandrogenism (Hollo et al., Lancet, 1357, 1976).

As a mechanism for the above-suggested role of both estrogens and androgens in osteoporosis, the presence of estrogen (Komm et al., Science 241: 81–84, 1988; Eriksen et al., Science 241: 84–86, 1988) as well as androgen (Colvard et al., Proc. Natl. Acad. Sci. 86: 854–857, 1989) receptors in osteoblasts could explain increased bone resorption observed after estrogen and androgen depletion.

While, in women, there is a rapid bone loss starting at menopause, bone loss in males can be recognized at about 65 years of age (Riggs et al., J. Clin. Invest. 67: 328–335, 1987). A more significant bone loss is seen in men at about 80 years of age, with the accompanying occurrence of hip, spine and wrist fractures. Several studies indicate that osteoporosis is a clinical manifestation of androgen deficiency in men (Baran et al., Calcif. Tissue Res. 26: 103–106, 1978; Odell and Swerdloff, West J. Med. 124: 446–475, 1976; Smith and Walker, Calif. Tissue Res. 22 (Suppl.): 225–228, 1976).

Therapy of postmenopausal women with nandrolone increased cortical bone mineral content (Clin. Orthop. 225: 273–277). Androgenic side-effects, however, were recorded in 50% of patients. Such data are of interest since while most therapies are limited to an arrest of bone loss, an increase in bone mass was found with the use of the anabolic steroid nandrolone. A similar stimulation of bone formation by androgens has been suggested in a hypogonadal male (Baran et al., Calcif. Tissue Res. 26: 103, 1978).

The decline with age of serum levels of DHEA-S and DHEA has led to the intriguing possibility that low serum DHEA and DHEA-S levels could be associated with cancer and cardiovascular diseases. In fact, a series of studies have indicated that subnormal levels of DHEA are associated with a high risk of breast cancer (Bulbrook et al., Lancet 2: 395–398, 1971; Rose et al., Eur. J. Cancer 13: 43–47, 1977; Thijssen et al., J. Steroid Biochem. 6: 729–734, 1975; Wang et al., Eur. J. Cancer 10: 477–482, 1974; Gomes et al., C. R. Acad. Sci. Paris 306: 261–264, 1978; Brownsez et al., Eur. J. Cancer 8: 131–137, 1972). Women with breast cancer were found to have low urinary levels of androsterone and etiocholanolone, two metabolites of DHEA (Bulbrook et al., Lancet 2:1238–1240, 1962; Cameron et al., Br. Med. J. 4: 768–771, 1970). Bulbrook et al. (Lancet 2: 1235–1240, 1962) then reported that women with primary operable breast cancer had urinary levels of 11-deoxy-17-ketosteroids (derived mainly from DHEA-S and DHEA) lower than normal, thus suggesting that a low secretion rate of DHEA and DHEA-S could precede the development of breast cancer.

The main approaches for the treatment of already developed breast cancer are related to the inhibition of estrogen action and/or formation. The role of estrogens in promoting the growth of estrogen-sensitive breast cancer has been recognized (Lippman, Semin. Oncol. 10 (Suppl. 4): 11–19, 1983; Sledge and McGuire, Cancer Res. 38: 61–75, 1984; Witliff, Cancer 53: 630–643, 1984; Poulin and Labrie, Cancer Res. 46: 4933–4937, 1986).

DHEA (450 mg/kg, b.w., 3 times a week) markedly delayed the appearance of breast tumors in C3H mice which were genetically bred to develop breast cancer (Schwartz, Cancer Res. 39: 1129–1132, 1979). Moreover, the risk of developing bladder cancer was found to be increased in men having lower serum DHEA levels (Gordon et al., Cancer Res. 51: 1366–1369, 1991).

Copending U.S. patent application Ser. No. 07/785,890 filed Nov. 4, 1991, relates to a method of treatment of breast and endometrial cancer in susceptible warm-blooded animals which may include inhibition of ovarian hormonal secretion by surgical means (ovariectomy) or chemical means (use of an LHRH agonist, e.g. [D-Trp$^6$, des-Gly-NH$_2^{10}$]LHRH ethylamide, or antagonist) as part of a combination therapy. Antiestrogens, androgens, progestins, inhibitors of sex steroid formation (especially of 17β-hydroxysteroid dehydrogenase- or aromarase-catalyzed production of sex steroids), inhibitors of prolactin secretion and of growth hormone secretion and ACTH secretion are discussed.

Copending U.S. patent application Ser. No. 07/724,532 filed on Jun. 28, 1991, relates to a method using low dose androgenic compounds for the prevention and treatment of breast cancer, endometrial cancer, osteoporosis and endometriosis.

Recent in vitro studies describe the relative antiproliferative activities of an androgen on the growth of the estrogen-sensitive human mammary carcinoma cell line ZR-75-1 (Poulin et al. "Androgens inhibit basal and estrogen-induced cell proliferation in the ZR-75-1 human breast cancer cell line", Breast Cancer Res. Treatm. 12: 213–225, 1989). As mentioned above, Poulin et al. (Breast Cancer Res. Treatm. 12: 213–225, 1989) have found that the growth of ZR-75-1 human breast carcinoma cells is inhibited by androgens, the inhibitory effect of androgens being additive to that of an antiestrogen. The inhibitory effect of androgens on the growth of human breast carcinoma cells ZR-75-1 has also been observed in vivo in nude mice (Dauvois and Labrie, Cancer Res. 51: 3131–3135, 1991).

DHEA has been suggested to have beneficial effects in obesity, diabetes, atherosclerosis, cancer, autoimmune diseases, fatigue, loss of muscle mass, connective tissue diseases, aging and longevity (Orentreich et al., J. Clin. Endocrinol. Metab. 59: 551–555, 1984; Regelson, Ann. N.Y. Acad. Sci. 521: 260–273, 1988; Gordon et al., Adv. Enzyme Regul. 26: 355–383, 1987; Schwartz, Adv. Cancer Res. 51: 391–423, 1988; Barrett-Connor et al., New Engl. J. Med. 315: 1519–1524, 1986).

In aged Sprague-Dawley rats, Schwartz (in Kent, Geriatrics 37: 157–160, 1982) has observed that body weight was reduced from 600 to 550 g by DHEA without affecting food intake. Schwartz (Cancer 39: 1129–1132, 1979) observed that C3H mice given DHEA (450 mg/kg, 3 times a week) gained significantly less weight and grew older than the control animals, had less body fat and were more active. The reduction in body weight was achieved without loss of appetite or food restriction. Furthermore, DHEA could prevent weight gain in animals bred to become obese in adulthood (in Kent, Geriatrics 37: 157–160, 1982).

DHEA in the diet has been shown to be a potent antihyperglycemic and antidiabetic agent in mice with inherited obesity-glucose intolerance syndrome (Coleman et al., Diabetes 33: 26–32, 1984).

DHEA reduced the incidence of atherosclerosis in cholesterol-fed rabbits (Gordon et al., J. Clin. Invest. 82: 712–720, 1988; Arad et al., Arteriosclerosis 9: 159–166, 1989). Moreover, high serum concentrations of DHEA-S have been reported to protect against death from cardiovascular diseases in men (Barrett-Connor et al., N. Engl. J. Med. 315: 1519–1524, 1986). Circulating levels of DHEA and DHEA-S have thus been found to be inversely correlated with mortality from cardiovascular disease (Barret-Connor et al., N. Engl. J. Med. 315: 1519–1524, 1986) and to decrease in parallel with the diminished immune competence (Thoman and Weigle, Adv. Immunol. 46: 221–222, 1989). A study in man has shown an inverse correlation between fetal serum DHEA-S and low density lipoprotein (LDL) levels (Parker et al., Science 208: 512, 1980).

In normal men, a placebo-controlled trial investigated the effect of daily oral administration of 1.6 g of DHEA for 28 days. Serum DHEA levels were increased 2.5- to 3.5-fold in the DHEA-treated group while total cholesterol and serum LDL cholesterol decreased by 7.1 and 7.5%, respectively (Nestler et al., J. Clin. Endocrinol. Metab. 66: 57–61, 1988). A decrease in body fat was found in 4 of the 5 men treated with DHEA for an average 31% decrease in percent of body fat with no change in total weight, thus suggesting a corresponding increase in muscle mass.

Drucker et al. (J. Clin. Endocrinol. Metab. 35, 48, 1972), Buster et al. (Am. J. Obstet. Gynecol. 166, 1163, 1992) and Welle et al. (J. Clin. Endocrinol. Metab., 71, 1259, 1990) have also administered DHEA orally to the human.

Obesity was found to be improved in the $A^{vy}$ mutant mouse (Yen et al., Lipids 12: 409–413, 1977) and in the Zucker rat (Cleary and Zisk, Fed. Proc. 42: 536, 1983). DHEA-treated C3H mice had a younger appearance than controls (Schwartz, Cancer Res. 39: 1129–1132, 1979).

Brain concentrations of DHEA are 6.5 times higher than corresponding concentrations in plasma (Lacroix et al., J. Steroid Biochem. 28: 317–325, 987). DHEA and DHEA-S improve memory in aging mice (Flood and Roberts, Brain Res. 448: 178–181, 1988). Serum DHEA-S concentrations in patients with Alzheimer disease have been found to be 48% lower on average than in age-matched controls (Sunderland et al., Lancet ii: 570, 1989). As mentioned above, DHEA administered chronically in the diet has been shown to increase longevity by delaying the development of some diseases in particular strains of animals.

U.S. Pat. No. 4,496,556 describes the use of DHEA or its derivatives to treat skin dryness by topical administration. Only local action on the sebaceous glands was described and no systemic action was observed.

U.S. Pat. No. 4,542,129 describes a topical composition for treating dry skin in a patient comprising the combination of DHEA and/or derivatives, a keratolytic agent and a non-toxic dermatologically acceptable vehicle.

Great Britain Patent No 1246639 describes preparation of esters of dehydroepiandrosterone for use as agents in the treatment of post and premenopause, tachycardia and headaches.

One problem facing the use of DHEA in humans is that high doses are required apparently because a large proportion of the compound is degraded in the liver before it reaches the blood stream after oral administration.

It is known that the efficiency of delivery of some drug can be improved by the use of certain pharmacologically inactive derivatives which are, by in vivo enzymatic or spontaneous reactions, transformed into the active drugs (see generally H. Bundgaard, Design and application of prodrugs. In A textbook of Drug Design and Development. Edited by P. Krogsgaard-Larsen and H. Bundgaard. Harwood Academic Publishers GmfH, Chur, Switzerland, 1991, pp. 113–191). For example, Druzgala et al., J. Steroid Biochem. Molec. Biol. 38, 149–154, 1991, describes prodrugs of glucocorticoids. Bodor et al. in U.S. patent application Ser. No. 4,213,978 and in German Patent Application Publication No DE 29 48 733 disclose the use of thiazolidine derivatives of progesterone as topical drugs. Percutaneous absorption of prodrug derivatives of estrogens and progestins are reported by Friend D. R. in Critical Reviews in Therapeutic Drug Carrier Systems, vol. 7 (2), pp. 149–186, 1990. Information about percutaneous absorption of drugs can also be found in Skin Permeability (H. Schaefer, A. Zesch and G. Stuttgen, eds), Springer-Verlag, Berlin, Heidelberg, New York, 1982, pp. 896.

Currently, low dose estrogen therapy is the standard approach used in perimenopausal and menopausal women to relieve vasomotor symptoms, urogenital atrophy, osteoporosis and other symptoms and signs associated with menopause (for review, see Edman, C. D., Estrogen Replacement Therapy. In: The menopause, Springer-Verlag, New York, (edited by H. J. Buchsbaum), pp. 77–84, 1983). Detailed information about the menopause and its therapy can be found in other chapters of this book. Obviously, such approaches limited to estrogen replacement therapy, associated or not with progestins, do not reproduce the equilibrium between estrogens and androgens that occurs naturally from the transformation of DHEA into its active metabolites in various target tissues.

Some esters of DHEA at position 3 are already described in the litterature (Riva et al., J. Org. Chem. 54: 3161–4, 1989; Parish and Chistrakorn, Synth. Commun. 15: 393–9, 1985; Rom Patent No RO 66924B; Jarosz and Zamojski, Tetrahedron 38:1453–6, 1982; Heublin et al., Z. Chem. 22: 178, 1982; German Patent Application No DE 2534911; Khaidem et al., Indian J. Chem. Sect. B, 27B: 850–1, 1988; Petit et al., J. Org. Chem. 52: 3573–8, 1987; Hanson and Reese, J. Chem. Soc. Perkin Trans. 1: 647–649, 1985); European Patent Application No 84–105741; Heublein et al., Acta Polym., 35: 673–7, 1984; Seevers et al., J. Med. Chem., 25: 1500–3, 1982; Yamashita and Kurosawa, Agric. Biol. Chem., 39: 2243–4, 1975; Japan Patent Application JP 50005372; Pohlmann et al., Mol. Cryst. Liquid Cryst. 13: 243–54, 1971.

Alkanesulfonates of DHEA is described as inhibitors of glucose-6-phosphate dehydrogenase activity in J. Pharm. Sci. 73: 1643–5, 1984.

In Britain Patent Application No GB 1246659 and S. Africa Patent Application No ZA 6806112 is disclosed DHEA esters for the treatment respectively of post and premenopause tachycardia and headaches and climateric complaints.

Leszczynski et al., in Biochem. Biophys. Acta, 1014: 90–7, 1989; idem: 1083: 18–28, 1991, have reported esterification of DHEA by blood plasma and Katz et al., in MCF-7 cell line in J. Steroid Biochem, 26: 687–92, 1987.

Ethyl carbonate of DHEA is reported by Weisz and Agocs in Arch. Pharm. (Weinheim, Ger), 319: 952–3, 1986.

Some halogeno esters of DHEA are described by Challis and Heap in J. Chromatogr. 50: 228–238, 1970 and by Pinelly and Nair in J. Chromatogr. 43: 223–228, 1969.

SUMMARY OF THE INVENTION

It is an object of the present invention to provide simple and efficient methods for systemic delivery of sex steroid precursors such as dehydroepiandiosterone, dehydroepiandrosterone sulfate and analogs which are converted in vivo to either DHEA or DHEA-S.

It is another object of the invention to provide novel treatments of menopause, vaginal atrophy, hypogonadism and diminished libido.

It is another object of the invention to provide kits and pharmaceutical compositions for use in accordance with the invention.

It is another object of the invention to provide novel sex steroid precursors and pharmaceutical compositions thereof.

In one aspect, the invention provides a method for treating menopause comprising administering to a patient in need of such treatment an effective amount of at least one sex steroid precursor selected from the group consisting of dehydroepiandrosterone, dehydroepiandrosterone sulphate, and compounds converted in vivo to either of the foregoing, in combination with an effective amount of an estrogen, a progestin or both.

In another aspect, the invention provides a pharmaceutical composition for the treatment of menopause comprising at least one sex steroid precursor selected from the group consisting of dehydroepiandrosterone, dehydroepiandrosterone sulphate, and compounds converted in vivo to either of the foregoing, and further comprising an estrogen or a progestin or both. One preferred combination is precursor and estrogen.

In another aspect, the invention provides a kit for the treatment of menopause having a first container which includes at least one sex steroid precursor selected from the group consisting of dehydroepiandrosterone, dehydroepiandrosterone sulphate, and compounds converted in vivo to either of the foregoing, and at least one additional container having either a progestin, an estrogen, or both. One preferred kit includes three containers having a precursor, an estrogen and a progestin, respectively, in separate containers.

In another aspect, the invention provides a method of treating vaginal atrophy, hypogonadism, diminished libido or reduced collagen or connective tissue in the skin comprising administering to a patient in need of such treatment an effective amount of a sex steroid precursor selected from the group consisting of dehydroepiandrosterone, dehydroepiandrosterone sulphate, and compounds converted in vivo to either of the foregoing.

In another aspect, the invention provides a therapeutic method of treating reduced or imbalanced concentrations of sex steroids comprising applying an effective amount of a pharmaceutical composition for percutaneous or transmucosal delivery to an outer surface of skin or mucosa of a patient in need of such treatment, said pharmaceutical composition comprising a carrier having dissolved therein at least one sex steroid precursor selected from the group consisting of dehydroepiandrosterone, dehydroepiandrosterone sulphate, and compounds converted in vivo to either of the foregoing, said precursor being present at a concentration of at least 7% by weight relative to the total pharmaceutical composition, and said carrier being compatible with skin or mucosa and allowing penetration of said precursor through said skin or mucosa, said carrier having sufficient viscosity to maintain said precursor on a localized area of skin or mucosa, without running or evaporating, for a time period sufficient to permit substantial penetration of said precursor through said localized area of said skin or mucosa. The foregoing method is useful in treating the conditions discussed above, menopausal symptoms and other conditions which respond to replenishment of diminished DHEA levels, including but not limited to obesity, cardiovascular disease, atherosclerosis, breast cancer, endometrial cancer, loss of muscle mass, diabetes, fatigue, connective tissue diseases and memory loss.

In another aspect, the invention provides a pharmaceutical composition for percutaneous or transmucosal delivery of said pharmaceutical composition comprising a carrier having dissolved therein at least one sex steroid precursor selected from the group consisting of dehydroepiandrosterone, dehydroepiandrosterone sulphate, and compounds converted in vivo to either of the foregoing, said precursor being present at a concentration of at least 7% by weight relative to the total pharmaceutical composition, and said carrier being compatible with skin or mucosa and allowing penetration of said precursor through said skin or mucosa, said carrier having sufficient viscosity to maintain said precursor on a localized area of skin or mucosa, without running or evaporating, for a time period sufficient to permit substantial penetration of said precursor through said localized area of said skin or mucosa.

In another aspect, the invention provides novel compounds (and pharmaceutical compositions containing them) of the formulas set forth below with substituent definitions set forth below:

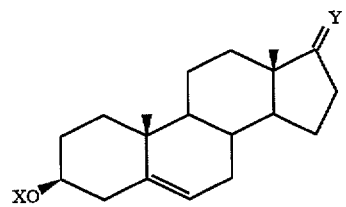

wherein X is selected from the group consisting of H,

$RCO_2CHR^a$— and $R^bSO_2$—

R being selected from the group consisting of hydrogen, straight- or branched-alkyl, straight- or branched-alkenyl, straight- or branched-alkynyl, aryl, furyl, straight- or branched-alkoxy, straight- or branched-alkenyloxy, straight- or branched-alkynyloxy, aryloxy, furyloxy and halogeno analogs of the foregoing $R^a$ being hydrogen or $(C_1-C_6)$ alkyl; and $R^b$ being selected from the group consisting of hydroxyl (or salts thereof), methyl, phenyl and p-toluyl;

wherein Y is a divalent ;substituted or unsubstituted moiety of the formula:

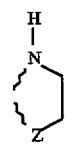

(Z being an oxygen or sulfur atom), and wherein Y and the carbon atom to which it is bonded together form a closed saturated 5-membered ring,

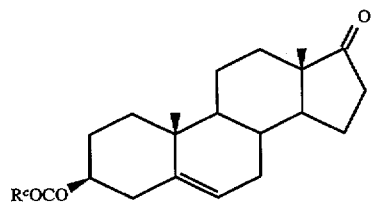

wherein $R^c$ is selected from the group consisting of $C_3-C_{20}$ straight- or branched-alkyl, $C_3-C_{20}$ straight- or branched-alkenyl, $C_3-C_{20}$ straight- or branched-alkynyl, aryl and halo-substituted analogs of the foregoing.

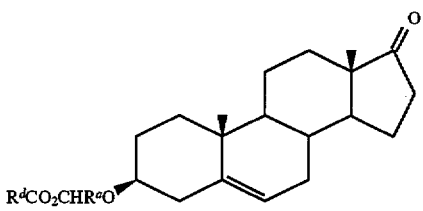

$R^d$ being selected from the group consisting of hydrogen, straight- or branched-alkyl, straight- or branched-alkenyl, straight- or branched-alkynyl, aryl, furyl, straight- or branched-alkoxy, straight- or branched-alkenyloxy, straight- or branched-alkynyloxy, aryloxy, furyloxy and halogeno analogs of the foregoing.

wherein $R_a$ is hydrogen or $(C_1-C_6)$ alkyl.

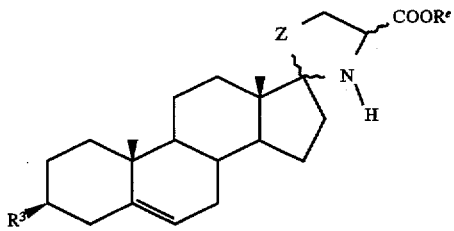

wherein $R^3$ is hydroxy or sulfate.
wherein $R^e$ is selected from the group consisting of hydrogen, benzyl, aryl, straight- or branched-alkyl, straight- or branched-alkenyl and straight- or branched-alkynyl.
wherein Z is oxygen or sulfur.

In one embodiment, a method is provided to compensate for the marked decrease in the secretion of the sex steroid precursors DHEA and DHEA-S by the adrenals during aging comprising administering DHEA, DHEA-S or analogs converted in vivo thereto in amounts which compensate for the consequences of decreased DHEA and DHEA-S secretion by the aging adrenals without exerting unwanted side effects.

It is believed that the methods of the invention are suitable for both prophylactic and therapeutic use. The serum concentrations, kits, and compositions discussed herein are equally useful toward either objective.

In another aspect, the invention provides a transdermal device comprising;

(a) a surface adapted for contact with human skin;

(b) a means of maintaining said surface on a localized area of skin to which said device is applied;

(c) a storage member in fluid communication with said surface, said member containing a pharmaceutical composition comprising a carrier and an active ingredient selected from the group consisting of dehydroepiandrosterone, dehydroepiandrosterone sulphate and analogues which are converted in vivo to either; and (d) a means for conducting said pharmaceutical composition from said storage member through said surface and into contact with said localized area of skin.

DETAILED DESCRIPTION OF THE PREFERRED EMBODIMENTS

To select patients who may benefit from the treatments described herein, the serum levels of DHEA and its metabolites can be measured as described by Belanger et al., in Steroid Formation, Degradation and Action in Peripheral, Normal and Neoplastic Tissues (H. Bradlow, L. Castagnetta, S. d'Aquino, L. Gogliotti, eds) Ann. N.Y. Acad. Sci. 586: 93–100, 1990; Haning et al., J. Clin. Endocrinol. Metab. 72: 1088, 1991. See also Labrie et al., Endocrinology 123, 1412–1417, 1988. Serum IGF-1 levels can be measured as described (Furlanetto et al., J. Clin. Invest. 60: 648, 1977).

In accordance with the invention, once the DHEA dificiency is determined, DHEA or its analogues is administered at a dosage sufficient to cause and maintain serum DHEA concentration between 4 and 7 micrograms per liter. When DHEA is administered by the preferred percutaneous or transmucosal technique, it has been found that DHEA is very efficiently absorbed into the blood to raise serum levels. For example, when a Glaxal cream, containing Glaxal base as a carrier available from Glaxal Canada Limited and 10% DHEA by weight of the total composition, is applied twice daily to a 100 square centimeter surface of the abdominal area in an amount providing 100 milligrams of active ingredient (e.g. DHEA), a typical patient is likely to respond with an increase of serum DHEA concentration of about 0.7 micrograms per liter per 50 kg of body weight. The delivered dosage may be raised or lowered in known manners by altering the location to which the lotion or ointment is applied, by altering the size of the surface area to which it is supplied, by altering the concentration of the active ingredient, or by altering the carrier. For example, increasing the surface area will normally increase the dosage of active ingredient delivered if the concentration of active ingredient remains constant. In the same manner, dosage delivered increases with increased concentration of active ingredient in the delivery base, and decreases with decreased concentration. Dosage delivered into the bloodstream also varies in a known manner with respect to the body region at which the transdermal penetration system is applied to the skin. Changing the carrier can also alter the delivered dosage in known ways. Preferably, serum DHEA concentration is measured before treatment begins, and a dosage is selected to quickly raise serum DHEA concentration to the preferred target range between 4 and 7 micrograms per liter. Subsequently, the patient is monitored both symptomatologically and by DHEA concentration to verify that the desired serum concentration target and symptomatic relief have been obtained. DHEA is then maintained a a constant concentration in the circulation. For a typical postmenopausal patient, for example, this dosage is the equivalent of application of 400 mg of the active precursor, as part of a 10 percent composition in Glaxal, to a 400 square centimeter area of the abdomen 2 times daily per 50 kg of body weight. If oral administration is chosen, 800 mg should be administered twice daily per 50 kg of body weight In accordance with the invention, DHEA, DHEA-S and/or compounds converted to either in vivo are utilized for the treatment of menopause, vaginal atrophy, hypogonadism, or diminished libido. Additionally, other conditions related to decreased secretion of DHEA by the adrenals during aging and which respond to DHEA therapy can be treated more efficiently with transdermally delivered DHEA, DHEA-S (or analogues) in accordance with the invention. Conditions expected to respond to the treatments herein may be diagnosed in conventional ways. For example, the appearance of breast cancer is usually detected by self breast examination, clinical breast examination by the physician and/or mammography. Endometrial cancer, on the other hand, is usually diagnosed by the PAP smear and/or endometrial biopsy. Both cancers can be diagnosed and evaluated by standard physical methods well known to those skilled in the art, e.g.

bone scan, chest X-Ray, skeletal survey, ultrasonography of the liver and liver scan (if needed), CAT scan, MRI and physical examination.

The first manifestations of menopause are usually hot flashes. Further characterization of menopause can be determined in accordance with known techniques. See for Example, The Menopause (Herbert J., Buchsbaurm, ed), Springer Verlag, New York (983), pp. 222.

Vaginal atrophy is often indicated by dyspareunia and vaginal infections. Vaginal atrophy, hypogonadism and diminished libido are all characterized in well-known ways. For the above-indicated diseases, see, for example, Korenman, Stanley G., "Sexual Dysfunctions" in Williams Textbook of Endocrinology (Jean D. Wilson and Daniel W. Foster, Eds.), W. B. Saunders Co, Philadelphia, pp. 1033-1048, 1992.

Bone density, on the other hand, can be measured by standard methods well known to those skilled in the art, e.g. QDR (Quantitative Digital Radiography), dual photon absorptiometry and computerized tomography. Plasma and urinary calcium and phosphate levels, plasma alkaline phosphatase, calcitonin and parathormone concentrations, as well as urinary hydroxyproline and calcium/creatinine ratios are useful parameters of bone formation and resorption.

Loss of collagen or connective tissues in the skin often accompanies aging, espedally in persons over 50 years of age. It may be evidenced by wrinkling of the skin and/or low elasticity.

Osteoporosis or otherwise insufficient bone mass, and other diseases treatable by activating the androgen receptor may be treated in accordance with the present invention or prophylactically prevented in accordance herewith. The present invention can aid in the prevention of breast or endometrial cancer.

The normal range of body weight is well known to those skilled in the art, while cholesterol and lipoproteins are routinely measured by standard techniques (Nestler et al. J. Clin. Endocrinol. Metab. 66: 57–61, 1988 for references).

Skin status can be assessed by visual inspection, palpation and, with more precision, by punch biopsy and standard histological examination.

In one preferred treatment for menopause, the invention seeks to simultaneously maintain blood levels of estrogen and a sex steroid precursor (e.g., DHEA or DHEA-S) within normal pre-menopausal parameters. The body converts DHEA-S to DHEA in most peripheral tissues. Without intending to be bound by theory, it is believed that maintenance of appropriate precursor levels will better enable natural enzymes, such as 17β-hydroxysteroid dehydrogenase, 3β-hydroxysteroidhydrogenase, aromarase and 5α-reductase to regulate production of androgens and estrogens and to maintain them in a manner more closely resembling their relative levels prevailing prior to menopause. Hence, the invention contemplates that not only estrogens but also androgens and precursors will be kept in better balance. In fact, all target tissues possess the enzymatic machinery necessary to synthesize androgen and/or estrogens according to local control and need (Labrie, Mol. Cell. Endocrinol. 78, C113–C118, 1991).

The estrogen and precursor (e.g., DHEA) when administered together in accordance with the invention may be administered simultaneously or separately. Indeed, the second active ingedient may be added to an existing estrogen therapy in order to achieve the combination therapy of the invention.

It is necessary only that both the estrogen and precursor be administered in a manner and at a dosage sufficient to allow blood serum concentration of each to obtain desired levels. In accordance with the combination therapy of the invention, concentration of the precursor is maintained within desired parameters at the same time that estrogen concentration is maintained within desired parameters. Where estradiol is used, serum estradiol concentration should typically be maintained between 50 and 300 nanograms per liter, preferably between 100 and 200 nanograms per liter and most preferably between 150 and 175 nanograms per liter. Where another estrogen is used, serum concentration may be varied in a known manner to account for the difference in estrogenic activity relative to estradiol and in order to achieve normal pre-menopausal estrogen levels. A lesser concentration is needed, for example, if Mestranol is used. Adequate serum estrogen levels can also be assessed by disappearance of the symptoms of menopause. Serum concentration of the second compound of the combination therapy (e.g., DHEA) is typically maintained between 4 and 7 micrograms per liter, preferably between 5 and 7 micrograms per liter, and most preferably between 6 and 7 micrograms per liter.

The estrogen is preferably estradiol, but may be sodium estrone sulfate or another compound which acts as an estrogen receptor agonist. When administered separately, commercially available estrogen supplements may be used, e.g., PREMARIN available from Ayerst (St-Laurent, Québec, Canada). One preferred precursor is DHEA, although DHEA-S and analogs discussed below are also especially effective for the reasons stated below. Where DHEA is used, for example, DHEA, pharmaceutical grade, is commercialy available from SIGMA (St-Louis, Mo., U.S.A.). For typical patients, the appropriate dosage of estrogen to achieve desired serum concentrations is between 0.3 and 2.5 milligrams of PREMARIN per day per 50 kg of body weight when administered orally. In certain embodiments of the invention, the estrogen may be 17β-estradiol administered percutaneously in a patch which is available from CIBA under the name ESTRADERM wherein the daily dose is between 0.05 and 0.2 milligrams per day per 50 kg of body weight. For typical patients, the appropriate dosage of the sex steroid precursor to achieve desired serum concentration of the precursor (or its metabolite where the precursor is converted in vivo to DHEA or DHEA-S) is between 0.25 and 2.5 grams per day per 50 kg of body weight when administered orally. The precursor may also be administered transdermally, as described in more detail below, in a sufficient amount to achieve target serum concentration. That correlation is also discussed in more detail below.

In another embodiment, menopause is treated with precursor as set forth above, in combination with periodic administration of a progestin such as medroxyprogesterone acetate (e.g. Provera) which is preferably administered intermittently, e.g. at a dosage of 5–10 mg per day for 10 consecutive days, said 10-day periods being spaced 20 days to 5 months a part. A combination therapy using a precursor, an estrogen and a progestin may also be used, preferably at the dosages discussed above for each component.

The sex steroid precursor used in the invention may be administered with or without additional carrier or diluent by the oral route but requires an additional carrier or diluent when administered by the preferred percutaneous or transmucosal route. In a pharmaceutical composition for oral administration, DHEA or other precursor is preferably present in a concentration between 5 and 98% by weight relative to total weight of the composition more preferably between 50 and 98 percent, especially between 80 and 98 percent. If estrogen such as estradiol is present, its concentration is preferably from 0.04 to 0.4 percent by weight. A single precursor such as DHEA may be the only active ingredient, or alternatively, a plurality of precursors and/or their analogues may be used (e.g., a combination of DHEA and DHEA-S, or a combination of two or more compounds converted in vivo to DHEA or DHEA-S, or a combination of DHEA and one or more analogues thereof which are converted to DHEA in vivo, etc. Where a combination is used, the total dosage of the sum of all precursors should be equal to the dosage range recited above for DHEA used alone, with appropriate adjustment for the different molecular weights of DHEA analogues such as DHEA esters. For example, if a DHEA ester is used instead of DHEA, dosage should be increased by a multiple equivalent to the ratio of the molecular weight of the DHEA ester to the molecular weight of DHEA. The blood level of DHEA is the final criteria of adequate dosage which takes into account individual variation in absorption and metabolism.

Preferably, the attending clinician will, especially at the beginning of treatment, monitor an individual patient's overall response and serum levels of both estrogen and DHEA (in comparison to the preferred serum concentrations discussed above), and monitor the patient's overall response to treatment, adjusting dosages as necessary where a given patients' metabolism or reaction to treatment is atypical. One approach would be to start treating with DHEA or its analogue(s) alone and to add the estrogen only if estrogen blood levels remain too low. Many patients may be treated only with the precursors of the invention without additional estrogen.

Treatment in accordance with the invention is suitable for indefinite continuation. It is expected that DHEA treatment will simply maintain DHEA levels within a range similar to that which occurs naturally in women before menopause (serum concentration between 4 and 7 micrograms per liter), or naturally in young adult men (serum concentration between 4 and 7 micrograms per liter). Accordingly, undesirable side effects from sustained DHEA treatment are expected to be either minimal or nonexistent. Avoiding side effects from sustained estrogen use may be achieved in ways already known to the art, for example, by intermittent administration of a progestin (e.g., medroxy-progesterone acetate) at a daily oral dose of 2 to 10 mg.

In order to facilitate the combination therapy of the invention, the invention contemplates pharmaceutical compositions which include both the estrogen and the second active compound (the precursor) in a single composition for simultaneous administration. The composition may be suitable for administration in any traditional manner including but not limited to oral administration, subcutaneous injection or intramuscular injection. In other embodiments, a kit is provided wherein the kit includes the estrogen and second compound (precursor(s)) in separate containers. In addition to other modes of administration, the second compound as well as the estrogen may also be administered transdermally in accordance with the invention as discussed in more detail below. Thus, the kit may include appropriate materials for transdermal administration, e.g., ointments, lotions, gels, creams, sustained release patches and the like.

Applicants have discovered that administration of DHEA has utility in the treatment of vaginal atrophy, hypogonadism and diminished libido, and improves the overall balance of circulating sex steroids, including estrogens and androgens. It is believed that the prior art has not previously suggested that these conditions respond to DHEA treatment. It is believed that DHEA, DHEA-S or a compound converted in vivo to either may be useful in the treatment of each of these three disorders.

Prior art methods for systemic administration of DHEA have included for oral and injection. Because DHEA treatments are often of prolonged and indefinite duration, repeated delivery by injection is very inconvenient. Oral administration, however, has proven relatively inefficient because orally administered DHEA goes first to the liver where a large percentage of it is prevented from entering the general circulation by local degradation.

We have recently observed that DHEA is very efficiently absorbed systemically in both males and females following application to the skin or mucosa (e.g. buccal, vaginal or rectal mucosa). We have discovered that therapeutically efficient doses of DHEA may be administered by the percutaneous or transmucosal route, thus avoiding first passage of the steroid through the liver as results from oral administration, and further avoiding the discomfort and inconvenience of administering DHEA by injection.

Accordingly, the present invention provides delivery systems for the administration of DHEA, DHEA-S and analogous compounds converted in vivo to either through the skin or mucosa. These systems are believed to be more efficient than oral administration because the liver is bypassed. These systems are also significantly less painful and more convenient than injections.

When DHEA, DHEA-S, or analogous compounds converted to DHEA or DHEA-S in vivo are formulated for transdermal penetration, any of a number of art-recognized transdermal penetration systems may be utilized. For example, DHEA may be prepared as part of an ointment, lotion, gel or cream for rubbing onto a patient's skin. Active ingredient is preferably present at from 7% to 20% by weight relative to the total weight of the pharmaceutical composition more preferably between 8 and 12%. Alternatively, the active ingredient may be placed into a transdermal patch having structures known in the art, for example, structures such as those set forth in E.P. Patent No. 0279982.

When formulated as an ointment, lotion, gel or cream or the like, the active compound is admixed with a suitable carrier which is compatible with human skin or mucosa and which enhances transdermal penetration of the compound through the skin or mucosa. Suitable carriers are known in the art and include but are not limited to Klucel HF and Glaxal base. Some are commercially available, e.g., Glaxal base available from Glaxal Canada Limited Company. Other suitable vehicles can be found in Koller and Buri, S.T.P. Pharma 3(2), 115–124, 1987. The carrier is preferably one in which the active ingredient(s) is (are) soluble at ambient temperature at the concentration of active ingredient that is used. The carrier should have sufficient viscosity to maintain the precursor on a localized area of skin or mucosa to which the composition has been applied, without running or evaporating for a time period sufficient to permit substantial penetration of the precursor through the localized area of skin or mucosa and into the bloodstream where it will cause a measurable and desired increase in serum DHEA concentration. The carrier is typically a mixture of several components, e.g. pharmaceutically acceptable solvents and a thickening agent. A mixture of organic and inorganic solvents can aid hydrophylic and lipophylic solubility, e.g. water and an alcohol such as ethanol. Desirably, the carrier is one which, if formulated as 10% DHEA and 90% carrier (by weight) and applied twice daily in an amount providing 100 mg of DHEA to the abdominal area, will elevate serum concentration of DHEA in a typical patient by at least 0.35 micrograms per liter per 50 kg of boby weight.

The carrier may also include various additives commonly used in ointments and lotions and well known in the cosmetic and medical arts. For example, fragrances, antioxidants, perfumes, gelling agents, thickening agents such as carboxymethylcellulose, surfactants, stabilizers, emollients, coloring agents and other similar agents may be present. When used to treat systemic diseases, the site of application on the skin should be changed in order to avoid excess local concentration of steroids and possible overstimulation of the skin and sebaceous glands by androgenic metabolites of DHEA.

The precursor can also be administered, in some instances, by the oral route, and may be formulated with conventional pharmaceutical excipients, e.g. spray dried lactose and magnesium stearate into tablets or capsules for oral administration at concentrations providing easy dosage in a range from 0.25 to 2.5 grams per day per 50 kg of body weight.

The active substance can be worked into tablets or dragee cores by being mixed with solid, pulverulent carrier substances, such as sodium citrate, calcium carbonate or dicaldum phosphate, and binders such as polyvinyl pyrrolidone, gelatin or cellulose derivatives, possibly by adding also lubricants such as magnesium stearate, sodium lauryl sulfate, "Carbowax" or polyethylene glycol. Of course, taste-improving substances can be added in the case of oral administration forms.

As further forms, one can use plug capsules, e.g. of hard gelatin, as well as closed solf-gelatin capsules comprising a softner or plasticizer, e.g. glycerine. The plug capsules contain the active substance preferably in the form of granulate, e.g. in mixture with fillers, such as lactose, saccharose, mannitol, starches, such as potato starch or amylopectin, cellulose derivatives or highly dispersed silicic acids. In solf-gelatin capsules, the active substance is preferably dissolved or suspended in suitable liquids, such as vegetable oils or liquid polyethylene glycols.

The concentration of active ingredient in the ointment, cream, gel or lotion is typically from about 7 to 20 percent preferably between 8 and 12 percent and most preferably 10 percent (by weight relative to the total weight of the lotion, cream, gel or ointment). Within the preferred ranges, higher concentrations allow a suitable dosage to be achieved while applying the lotion, ointment, gel or cream to a lesser surface area of the skin than would be possible at lower concentrations and allows more freedom in choosing the body parts to which the ointment or lotion will be applied. For example, it is well known in the art that a compound which is capable of transdermal penetration normally penetrates more efficiently at some points in the body than in others. For example, penetration is very efficient on the forearm and considerably less effident on the palms.

The lotion, ointment, gel or cream should be thoroughly rubbed into the skin so that no excess is plainly visible, and the skin should not be washed in that region until most of the transdermal penetration has occurred preferably at least 15 minutes and, more preferably, at least 30 minutes.

A transdermal patch may be used to deliver precursor in accordance with known techniques. It is typically applied for a much longer period, e.g., 1 to 4 days, but typically contacts active ingredient to a smaller surface area, allowing a slow and constant delivery of active ingredient.

A number of transdermal drug delivery systems that have been developed, and are in use, are suitable for delivering the active ingredient of the present invention. The rate of release is typically controlled by a matrix diffusion, or by passage of the active ingredient through a controlling membrane.

Mechanical aspects of transdermat devices are well known in the rat, and are explained, for example, in U.S. Pat. Nos. 5,162,037, 5,154,922, 5,135,480, 4,666,441, 4,624,665, 3,742,951, 3,797,444, 4,568,343, 5,064,654, 5,071,644, 5,071,657, the disclosures of which are incorporated herein by reference. Additional background is provided by European Patent 0279982 and British Patent Application 2185187.

The device may be any of the general types known in the art including adhesive matrix and reservoir-type transdermal delivery devices. The device may include drug-containing matrixes incorporating fibers which absorb the active ingredient and/or carrier. In a reservoir-type device, the reservoir may be defined by a polymer membrane impermeable to the carrier and to the active ingredient.

In a transdermal device, the device itself maintains active ingredient in contact with the desired localized skin surface. In such a device, the viscosity of the carrier for active ingredient is of less concern than with a cream or gel. A solvent system for a transdermal device may include, for example, oleic add, linear alcohol factate and dipropylene glycol, or other solvent systems known in the art. The active ingredient may be dissolved or suspended in the carrier.

For attachment to the skin, a transdermal patch may be mounted on a surgical adhesive tape having a hole punched in the middle. The adhesive is preferably covered by a release liner to protect it prior to use. Typical material suitable for release includes polyethylene and polyethylene-coated paper, and preferably silicone-coated for ease of removal. For applying the device, the release liner is simply peeled away and the adhesive attached to the patient's skin. In U.S. Pat. No. 5,135,480, the disclosure of which is incorporated by reference, Bannon et al. describe an alternative device having a non-adhesive means for securing the device to the skin.

The target serum concentration of DHEA is the same, regardless of whether sex steroid precursor is being used as part of a combination therapy for treatment of menopause or is being used for the treatment of skin deterioration, vaginal atrophy, hypogonadism or diminished libido in accordance with the invention or for the treatment of a wide variety of conditions related to decreased secretion of DHEA by the adrenals. It is pointed out that dosage of DHEA, DHEA-S or any analog discussed herein can all be correlated to a target serum concentration of DHEA because all are converted in vivo, either directly or indirectly, into DHEA.

The percutaneous or transmucosal delivery system of the invention may also be used as a novel and improved delivery system for the prevention and/or treatment of osteoporosis or other diseases which respond favorably to treatment with DHEA. The desired target serum levels for these latter purposes is also the same as indicated above.

DHEA used for percutaneous or transmucosal application can be in the form of the free alcohol or of one or more of its derivatives, e valerate, benzoate, acetate, enanthate and fatty ester derivatives. The delivery of DHEA or of its analogues through the skin is an acceptable, comfortable and noninvasive way of administering such compound. It also avoids gastrointestinal irritation and degradation of the compound and toxicologic problems due to first passage through the liver before reaching the general circulation.

One method for preventing or inhibiting growth of breast and endometrial carcinoma cells is activation of the androgen receptor with an effective compound having an affinity for the receptor site such that it binds to the androgen receptor at low concentrations while not significantly activating other classes of steroid receptors linked to potential side effects.

Since DHEA is a natural source of androgens (Labrie, Mol. Cell. Endocrinol. 78: C113–C118, 1991) and the secretion of this compound markedly decreases during aging, its replacement should have minimal unwanted side effects.

Percutaneous or transmucosal delivery of DHEA in accordance with the invention thus provides a novel method for prevention and therapy of diseases responsive to activation of the androgen receptor, e.g. bone loss, obesity, breast cancer, endometrial cancer, hypogonadism, loss of libido, loss of muscle mass, loss of energy, and other aging processes. The invention is also useful for many diseases wherein activation of the estrogen receptor will have beneficial effects, especially osteoporosis and vaginal atrophy.

EXAMPLES OF SOME PREFERRED DERIVATIVES

Derivatives of DHEA or DHEA-S in accordance with the present invention may be made by the following approaches:
- Esterification of the 3β function into an ester which can be cleaved by esterase (the cleavage does not generate toxic substances) and transformation of the 17-keto group into oxazolidine or thiazoliodines which are unstable in the body and regenerate a natural precursor.
- Formation at position 3β of an α-acyloxyalkyl ether which can be cleaved by esterase into an unstable hemiacetal. The decomposition of this hemiacetal regenerates the natural precursor.
- Without modification of the 3β function, transformation of the 17-keto group into oxazolidine or thiazoliodines which are unstable in the body and regenerate DHEA or DHEA-S.

The compounds disclosed below are expected to convert in vivo into dehydroepiandrosterone (DHEA) or dehydroepiandrosterone-sulfate

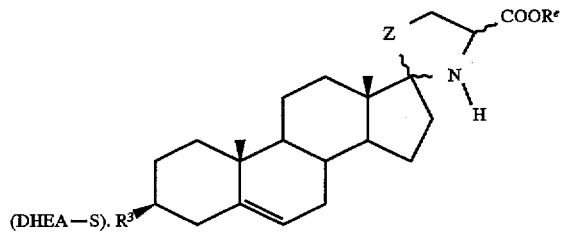

wherein $R^3$ is hydroxy or sulfate.
wherein $R^e$ is selected from the group consisting of hydrogen, benzyl, aryl, straight- or branched-alkyl, straight- or branched-alkenyl and straight- or branched-alkynyl.
wherein Z is oxygen or sulfur.

Some derivatives of DHEA being more lipophilic than DHEA itself can be stocked in skin fat and advantageously release DHEA slowly over time.

In some preferred compounds of the invention, the function at position 3 is an ester of sulfuric acid (or salts thereof), formic acid, acetic acid, benzoic acid, butyric acid, decanoic acid, enanthic acid, furoic acid, heptanoic acid, isocaproic acid, undecanoic acid, undecylenic acid, palmitic acid, phenylpropionic acid, pivalic acid, propionic acid, valeric acid, carbonic acid (preferably ethylcarbonate or benzylcarbonate).

In some preferred compounds of the invention, DHEA (or DHEA-S) is modified by a 17-substituent of the following formula:

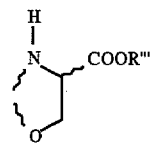

or

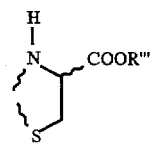

wherein R''' is selected from the group consisting of hydrogen, benzyl, straight- or branched-alkyl and straight- or branched-alkenyl.

Certain preferred 3β-ester derivatives of DHEA are listed below:

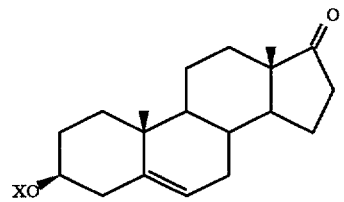

| COMPOUNDS | X |
|---|---|
| dehydroepiandrosterone-3β-formate | HCO |
| dehydroepiandrosterone-3β-acetate | $CH_3CO$ |
| dehydroepiandrosterone-3β-propionate | $CH_3CH_2CO$ |
| dehydroepiandrosterone-3β-butyrate | $CH_3(CH_2)_2CO$ |
| dehydroepiandrosterone-3β-valerate | $CH_3(CH_2)_3CO$ |
| dehydroepiandrosterone-3β-pivalate | $(CH_3)_3CCO$ |
| dehydroepiandrosterone-3β-benzoate | $C_6H_5CO$ |
| dehydroepiandrosterone-3β-furoate | $C_4H_3OCO$ |
| dehydroepiandrosterone-3β-cypionate | $C_5H_9(CH_2)_2CO$ |
| dehydroepiandrosterone-3β-lactate | $CH_3CHOHCO$ |
| dehydroepiandrosterone-3β-decanoate | $CH_3(CH_2)_8CO$ |
| dehydroepiandrosterone-3β-undecanoate | $CH_3(CH_2)_{10}CO$ |
| dehydroepiandrosterone-3β-palmitate | $CH_3(CH_2)_{14}CO$ |
| dehydroepiandrosterone-3β-ethylcarbonate | $C_2H_5OCO$ |
| dehydroepiandrosterone-3β-benzylcarbonate | $C_6H_5CH_2OCO$ |
| dehydroepiandrosterone-3β-isocaproate | $(CH_3)_2(CH_2)_3CO$ |
| dehydroepiandrosterone-3β-undecylenate | $H_2C=CH(CH_2)_8CO$ |
| dehydroepiandrosterone-3β-enanthate | $CH_3(CH_2)_5CO$ |
| dehydroepiandrosterone-3β-phenylpropionate | $C_6H_5(CH_2)_2CO$ |
| 3β-hydroxymethoxy-5-androsten-17-one acetate | $CH_3CO_2CH_2$ |
| 3β-hydroxymethoxy-5-androsten-17-one decanoate | $CH_3(CH_2)_8CO_2CH_2$ |

Some other preferred DHEA derivatives are listed below:

| COMPOUNDS | R''' | Z |
|---|---|---|
| 3β-hydroxy-5-androstene-17-spiro(1',3'-thiazolidine-4'-ethyl carboxylate) | $C_2H_5$ | S |
| 3β-hydroxy-5-androstene-17-spiro(1',3'-thiazolidine-4'-benzyl carboxylate) | $C_6H_5CH_2$ | S |
| 3β-hydroxy-5-androstene-17-spiro(1',3'-thiazolidine-4'-hexyl carboxylate) | $C_6H_{13}$ | S |
| 3β-hydroxy-5-androstene-17-spiro(1',3'-oxazolidine-4'-ethyl carboxylate) | $C_2H_5$ | O |
| 3β-hydroxy-5-androstene-17-spiro(1',3'-oxazolidine-4'-benzyl carboxylate) | $C_6H_5CH_2$ | O |
| 3β-hydroxy-5-androstene-17-spiro(1',3'-oxazolidine-4'-hexyl carboxylate) | $C_6H_{13}$ | O |

Corresponding 17-substituted analogs of DHEA-S may also be used.

EXAMPLES OF SYNTHESIS

Example 1

3β-formyloxy-5-androsiene-17-one

Following the procedure described by Ringold (H. J. Ringold, et al., J. Am. Chem. Soc. 78, 816, 1956), dehydroepiandrosterone (2.88 g, 10 mmol) dissolved in 85% formic acid (100 mL) is heated at 60° C. for 1 h. After cooling, the mixture is poured into iced water and after 16 h, crystals are filtered and dried in vacuo.

Example 2

3β-acetoxy-5-androstene-17-one

Dehydroepiandrosterone (2.88 g, 10 mmol) is dissolved in a mixture (100 ml) of anhydride acetic and pyridine (1:1 v/v) and left at room temperature for 16 h. The mixture is then poured carefully into iced water and after 16 h, crystals are filtered and dried in vacuo.

Example 3

Dehydroepiandrosterone-3β-undecanoate

A solution of undecanoyl chloride (10.2 g, 50 mmol) in $CH_2Cl_2$ (50 ml) was added to a mixture of 5-androsteno3β-ol-17-one (11.53 g, 40 mmol), $Et_3N$ (14 ml, 100 mmol) and dimethylaminopyridine (0.6 g, 5 mmol) in $CH_2Cl_2$ (150 ml) at 5° C. After addition, the mixture was stirred overnight at room temperature. The $CH_2Cl_2$ layer was washed successively with water, 2N HCl (twice), 5% $K_2CO_3$ (twice), brine and dried. Removal of the solvent gave the crude product which was recrystallized with a mixture of n-hexane:benzene to give the pure product (13.66 g; 75%), M.P. 84°–85° C.; $^1$H-NMR ($CDCl_3$); δ 0.83–0.86 (m, 6H, $C_{18}$—$CH_3$ and $CH_3$); 1.03 (s, 3H, $C_{19}$—$CH_3$); 4.58–4.61 (m, 1H, $C_3$—H); 5.37 (d, 1H, vinyl, J=4.89 Hz). $^{13}$C-NMR ($CDCl_3$) δ: 220.90, 179.25, 139.99, 121.78, 73.38, 51.69, 50.14, 47.49, 38.12, 36.94, 36.72, 35.81, 34.68, 31.87, 31.47, 31.42, 30.76, 29.53, 29.44, 29.27, 29.23, 29.09, 27.73, 25.03, 22.66, 21.86, 20.31, 19.33, 14.09, 13.53.

Example 4

3β-acyloxy-5-androstene-17-one

The above esters at position 3β of dehydroepiandrosterone are prepared as follows:

Dehydroepiandrosterone (10 mmol) is dissolved in pyridine (50 mL) and added to a solution of acyl chloride (prepared from the corresponding acid and oxalyl chloride) in the same solvent (50 mL). Dimethylaminopyridine (10%) is then added and the mixture is left at room temperature for 16 h. The mixture is then carefully poured into iced water and extracted with ethyl acetate. The organic phase is washed with diluted HCl, water, saturated sodium bicarbonate and water, dried and evaporated to dryness to give the ester.

Example 5

3β-benzyloxycarbonyloxy-5-androsten-17-one

To a stirred solution of dehydroepiandrosterone (2.88 % 10 mmol) in methylene chloride (100 mL) is added dropwise benzylchloroformate, over a period of 30 min following the known procedure (F. Reber and T. Reichstein, Helv. Chim. Acta, 28, 1164, 1945). After stirring for 3 h, the mixture is washed with water and evaporated to dryness. The residue is then dissolved in acetone and precipitated in iced water. After 16 h, crystals are filtered and dried in vacuo.

Example 6

3β-ethoxyoxycarbonyloxy-5-androsten-17-one

Same procedure as described in example 5 except that ethylchloroformate is used instead of benzylchloroformate.

Example 7

3β-hydroxy-5-androstene-17-spiro-2'-(1',3'-thiazolidine-4'-ethyl carboxylate)

Following the procedure described by Djerassi (C. Djerassi, N. Crossley and M. A. Kielczewski, J. Org. Chem. 27, 1112, 1962), dehydroepiandrosterone (2.88 g, 10 mmol) is dissolved in anhydrous ethanol, sodium acetate is added followed by L-cysteine ethyl ester hydrochloride (18 g, 100 mmol) and the mixture is heated overnight under an argon atmosphere. The reaction mixture is then evaported under vacuum. Methylene chloride is added to predpitate excess of L-cysteine ethyl ester hydrochloride . The solution is then filtered and the filtrate is washed twice with water, dried on magnesium sulfate, filtered and evaporated under vacuum. The residue is triturated with ethanol to give crystals.

Example 8

3β-hydroxy-5-androstene-17-spiro-2'-(1', 3'-thiazolidine-4'-benzyl carboxylate)

Same procedure as described in example 7 except that L-cysteine benzyl ester hydrochloride is used instead of L-cysteine ethyl ester hydrochloride.

Example 9

3β-hydroxy-5-androstene-17-spiro-2'-(1',3'-thiazolidine-4'-alkyl carboxylate)

Same procedure as described in example 7 except that different L-cysteine alkyl esters hydrochloride (e.g. L-cysteine hexyl ester hydrochloride) are used instead of L-cysteine ethyl ester hydrochloride.

Example 10

3β-hydroxy-5-androstene-17-spiro-2'-(1',3'-oxazolidine-4'-ethyl carboxylate)

The same procedure as described in the Example 7 is used except the oxazolidine derivative is prepared using serine ethyl ester hydrochloride instead of L-cysteine ethyl ester hydrochloride.

Example 11

3β-hydroxy-5-androstene-17-spiro-2'-(1',3'-oxazolidine-4'-benzyl carboxylate)

Same procedure as described in example 10 except that serine benzyl ester hydrochloride is used instead of serine ethyl ester hydrochloride.

Example 12

3β-hydroxy-5-androstene-17-spiro-2'-(1',3'-oxazolidine-4'-alkyl carboxylate)

Same procedure as described in example 10 except that different serine alkyl esters hydrochloride (e.g. serine hexyl ester hydrochloride) are used instead of serine ethyl ester hydrochloride.

Example 13

3β-hydroxymethoxy-5-androsten-17-one acetate

To a solution of dehydroepiandrosterone (2.88 g, 10 mmol) in THF (100 mL) is added sodium hydride (11 mmol, 60% in oil) at room temperature under an argon atmosphere. When all the sodium hydride has reacted, chloromethyl acetate (prepared from acetyl chloride and formaldehyde (or derivative) using $ZnCl_2$ as catalyst) is added and the mixture is heated for a few hours. After cooling, the mixture is poured into water and extracted with ethyl acetate. The organic phase is then washed with water, dried, filtered and evaporated to dryness to give the desired compound.

EXAMPLES OF PHARMACEUTICAL COMPOSITIONS

In one aspect, the present invention involves applying DHEA (or its analogues) formulation to the skin or other epithelial tissue for a time period sufficient to permit sufficient penetration of the compound for systemic or topical action, as desired. The composition may be applied as a gel, a cream, an ointment, a lotion or the like or may involve use of a delivery system as described in U.S. Pat. Nos. 3,742,951, 3,797,494 or 4,568,343. Devices as described in U.S. Pat. Nos. 5,064,654, 5,071,644 or 5,071,657 can also be used to facilitate steroid absorption.

All the pharmaceutical compositions of the present invention may contain appropriate preservatives known in the art.

The following non-limiting examples describe the preparation of a typical cream, lotion, gel and ointment, respectively. In addition to these vehicles, one skilled in the art may choose other vehicles in order to adapt to specific dermatologic needs.

Example 14

A typical lotion contains (W/W) 10% DHEA, 15% propylene glycol and 70% ethanol and water 5%.

Example 15

A typical gel contains (W/W) 10% DHEA, 5% propylene glycol, 0.2% Carbomer 940 (available as Carbopol 940$^R$ from B. F. Goodrich), 40% water, 0.2% triethanolamine, 2% PFG-12-Buteh-16 (available as Ucon$^R$ fluid 50 from Union Carbide), 1% hydroxypropyl and 41.6% ethanol (95% ethanol-5% water).

Example 16

A typical ointment contains (W/W) 10% DHEA, 13% propylene glycol, 74% petrolatum, 2.9% glycerylmonostearate and 0.1% polylparaben.

Example 17

A typical cream contains (W/W) 10% DHEA, 0.2% propylparaben, 5% lanolin oil, 7.5% sesame oil, 5% cetyl alcohol, 2% glyceryl monostearate, 1% triethanolamine, 5% propylene glycol, 0.1% Carbomer 940$^R$ and 64.2% water.

DHEA permeability can be enhanced by various techniques in order to reduce the dose used. Methods and compositions for enhancing permeability of an active compound can be found, for example, in U.S. Pat. Nos. 5,051,260, 4,006,218, 3551,554, 3,472,931, 4,568,343, 3,989,816 and 4,405,616.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A method for inhibiting the development of, or treating, diminished libido comprising administering to a patient in need of such treatment an amount of at least one sex steroid precursor selected from the group consisting of dehydroepiandrosterone, dehydroepiandrosterone sulfate, and compounds converted in vivo to either of the foregoing, effective to maintain serum DHEA levels in said patient at between 4 and 13 micrograms per liter.

2. The method of claim 1 wherein said precursor is administered percutaneously or transmucosally.

3. The method of claim 1 wherein said precursor is administered percutaneously or transmucosally by applying a pharmaceutical composition containing said precursor at a concentration of at least 7% by weight relative to the total pharmaceutical composition.

* * * * *